United States Patent
Averill et al.

[11] Patent Number: 5,882,666
[45] Date of Patent: Mar. 16, 1999

[54] SKIN CARE COMPOUNDS AND PREPARATION THEREOF

[76] Inventors: Robert G. Averill; Miriam Averill, both of P.O. Box 105, 400 County Rd., Montpelier, Vt. 05601

[21] Appl. No.: 975,191

[22] Filed: Nov. 20, 1997

[51] Int. Cl.⁶ ...................................................... A61K 7/00
[52] U.S. Cl. .................. 424/401; 424/78.05; 424/78.06; 514/887; 514/847; 514/846
[58] Field of Search ............................................... 424/401

[56] References Cited

U.S. PATENT DOCUMENTS

| 5,759,555 | 6/1998 | Moy | 424/401 |
| 5,776,441 | 7/1998 | Scancarella | 424/61 |

*Primary Examiner*—Thurman K. Page
*Assistant Examiner*—D. Faulkner
*Attorney, Agent, or Firm*—Thomas N. Neiman

[57] ABSTRACT

It has long been the practice to treat the skin of individuals to clean and soften the skin with soaps and detergents. A compound containing glycerin, alcohol, jojoba oil, aloe vera, silk extracts, glyceryl monostearate, decyl oleate, propylene glycol, isopropyl palmitate, dimethicone, magnesium ascorbyl phosphate, sodium dodecyl sulfate, methyl paraben, xanthan gum, propyl paraben, and deionized water are formed into a silk cream composition in order to clean and soften skin. A lotion form of the compound that adds natural fragrances and mineral oil is also disclosed. A method of using the skin cream and or the lotion is also disclosed.

7 Claims, No Drawings

SKIN CARE COMPOUNDS AND PREPARATION THEREOF

BACKGROUND OF THE INVENTION

This invention pertains to skin care compounds and, in particular, to such skin care compounds that are designed to clean and restore the skin of the individual user by providing a compound using a silk oil protein to repair damaged and promote smooth supple skin.

There have been many different compounds used for cleaning and restoring skin that have been used over the years to treat the skin. The sale of beauty products is a very large business and all sorts of compounds have been used for this purpose. Recently, the use of natural products has been coming into vogue at this time. Skin repair products having aloe vera, soaps, detergents, and the like, are commonly used in the field. What is needed are skin compounds that use the natural oil of silk to clean and restore and repair the skin of the users of the product.

Clearly, it is desirable for a skin care compound of this type to be very effective and easy to use. It is an object of this invention to set skin care compounds weight which avoids the disadvantages of previous skin care products.

SUMMARY OF THE INVENTION

Particularly, it is the object of this invention to set forth a skin care compound, for use in helping the individual user's skin by softening, minimizing the effects of sunburn and chapping and reducing the effects of lesions and cracked skin, consisting of a mixture of glycerin, alcohol, jojoba oil, aloe vera, silk extracts, glycercyl monostearate, decyl oleate, propylene glycol, isopropyl palmitate, dimethicone, magnesium ascorbyl phosphate, sodium dodecyl sulfate, methyl paraben, xanthan gum, propyl paraben and water; an approximate proportion of ten percent or less of glycerin; an approximate proportion of ten percent or less of alcohol; an approximate proportion of six percent or less of jojoba oil; an approximate proportion of six percent or less of aloe vera; an approximate proportion of six percent or less of silk extracts; an approximate proportion of five percent or less of glyceryl monostearate; an approximate proportion of three percent or less of decyl oleate; an approximate proportion of three percent or less of propylene glycol; an approximate proportion of three percent or less of isopropyl palmitate; an approximate proportion of two percent or less of dimethicone; an approximate proportion of two percent or less of magnesium ascorbyl phosphate; an approximate proportion of one percent or less of sodium dodecyl sulfate; an approximate proportion of one percent or less of methyl paraben; an approximate proportion of one percent or less of xanthan gum; an approximate proportion of one percent or less of propyl paraben; and the balance of the compound in the form of water to complete the compound. It is also the object of this invention to teach a skin care compound, for use in cleaning the skin of the skin of an individual user by cleaning and softening the skin consisting of a mixture of mineral oil, glycerin, alcohol, glyceryl monostearate, stearic acid, silk abstract, polyoxythylen stearether, methyl paraben, natural fragrance, propyl paraben, and water; an approximate proportion of twenty percent or less of mineral oil; an approximate proportion of ten percent or less of glycerin; an approximate proportion of five percent or less of alcohol; an approximate proportion of five percent or less glyceryl monostearate; an approximate proportion of three percent or less of silk extract; an approximate proportion of three percent or less polyoxyethylen stearylether; an approximate proportion of two percent or less methyl paraben; an approximate proportion of two percent or less of natural fragrance; an approximate proportion of two percent or less of propyl paraben; and the balance of the compound in the form of water to complete the compound.

BRIEF DESCRIPTION OF THE INVENTION

Further objects and features of this invention will become more apparent by reference to the following description.

DESCRIPTION OF THE PREFERRED EMBODIMENT

The parts and the percentage figures are expressed on a weight basis throughout the specification. The preferred embodiment of the skin cream was prepared as follows;

| Chemical | Percentage |
| --- | --- |
| Glycerin: | 8.00 |
| Stearyl Alcohol: | 8.00 |
| Jojoba Oil: | 5.00 |
| Aloe Vera: | 5.00 |
| Silk Extracts: | 5.00 |
| Glyceryl Monostearate: | 4.00 |
| Decyl Oleate: | 2.00 |
| Propylene Glycol: | 2.00 |
| Isopropyl Palmitate: | 2.00 |
| Dimethicone: | 1.00 |
| Magnesium Ascorbyl Phosphate: | 1.00 |
| Sodium Dodecyl Sulfate: | 0.50 |
| Methyl Paraben: | 0.15 |
| Xanthan Gum: | 0.10 |
| Propyl Paraben: | 0.05 |
| Deionized Water: | add to 100 percent |

Glycerin, glyceryl monostearate, propylene glycol are forms of glycerol which is a colorless liquid that absorbs moisture and is used in the manufacture of cosmetics. Jojoba oil is a liquid wax extract from the jojoba plant found in the deserts of the southwest and in Mexico. It is similar to vegetable oil and has many of the characteristics of sperm whale oil. Aloe Vera is an oil used extensively in products designed for healing skin. The silk extracts incorporated in the compound are processed in the working of the cocoon extract of the silk thread. The cocoon is boiled and a creamy substance boils off. The oils from the cocoon and worm are the silk protein which contains many amino acids. The oil has many of the properties that are exhibited by the silk thread itself. The effect on the skin of this cream compound is that the smoothness of the skin is enhanced and any damage, such as dryness, chapping, sunburn or the like, on the surface of the skin is minimized and a fast improvement is achieved.

The parabens (ethyl and propyl) used are compounds of esters of para-hydroxybenzoic acid and have been shown to effective antimicrobial agents as well as being effective against molds and yeasts. Isopropyl palminate is a form of palmitic acid that is often used to form a soap product and is often combined with decyl oleate and sodium dodecyl sulfate for that purpose. Xanthan gum is a product used for its stabilizing and emulsifying properties. It is a polysaccharide that is readily soluble in hot or cold water and imparts a high viscosity at low concentrations. The water used to complete the compound is deionized to minimize any problems of purification of the product.

The skin cream product is used by applying the skin cream to the hands and face. Massage in gently and then rinse with cold water. The cleansing lotion is designed to clean the skin and remove make up and mascara easily without scrubbing. The perferred embodiment in formulating the cleansing lotion is as follows;

| Chemical | Percentage |
|---|---|
| Mineral Oil: | 15.00 |
| Glycerin: | 8.00 |
| Stearyl Alcohol: | 2.50 |
| Glyceryl Monostearate: | 2.00 |
| Stearic Acid: | 1.50 |
| Silk Extract: | 1.00 |
| Polyoxyethylen Stearylether: | 1.00 |
| Methyl Paraben: | 0.15 |
| Natural Fragrance; | 0.10 |
| Propyl Paraben: | 0.05 |
| Deionized Water: | add to 100.00 |

The mineral oil is designed to provide a smoothing and spreading agent. The stearic acid is soluble in ether and used in soap products. The polyoxyethylen stearylether acts as a solvent for the compound. The other items in the compound have been described previously.

While we have described our invention in connection with specific embodiments thereof, it is clearly to be understood that this is done only by way of example and not as a limitation to the scope of our invention as set forth in the objects thereof and in the appended claims.

We claim:

1. A skin care composition, for use in helping the individual user's skin by softening, minimizing the effects of sunburns and chapping and reducing the effects of lesions and cracked skin, consisting of:
    a mixture of glycerin, alcohol, jojoba oil, aloe vera, silk extracts, glycercyl monostearate, decyl oleate, propylene glycol, isopropyl palmitate, dimethicone, magnesium ascorbyl phosphate, sodium dodecyl sulfate, methyl paraben, xanthan gum, propyl paraben and water;
    an approximate proportion of ten percent or less of glycerin;
    an approximate proportion of ten percent or less of alcohol;
    an approximate proportion of six percent or less of jojoba oil;
    an approximate proportion of six percent or less of aloe vera;
    an approximate proportion of six percent or less of silk extracts;
    an approximate proportion of five percent or less of glyceryl monostearate;
    an approximate proportion of three percent of less of decyl oleate;
    an approximate proportion of three percent or less of propylene glycol;
    an approximate proportion of three percent or less of isopropyl palmitate;
    an approximate proportion of two percent or less of dimethicone;
    an approximate proportion of two percent or less of magnesium ascorbyl phosphate;
    an approximate proportion of one percent or less of sodium dodecyl sulfate;
    an approximate proportion of one percent or less of methyl paraben;
    an approximate proportion of one percent or less of xanthan gum;
    an approximate proportion of one percent or less of propyl paraben; and
    the balance of the compound in the form of water to complete the compound.

2. A skin care composition, according to claim 1, wherein:
    said approximate proportion or less than ten percent of alcohol comprises the use of stearyl alcohol.

3. A skin care composition, according to claim 1, wherein:
    said balance of the compound in the form of water to complete the compound comprises the use of deionized water.

4. A skin care composition, for use cleaning the skin of the individual user by cleaning and softening the skin, consisting of:
    a mixture of mineral oil, glycerin, alcohol, glyceryl monostearate, stearic acid, silk extract, polyoxyethylen stearylether, methyl paraben, natural fragrance, propyl paraben and water;
    an approximate proportion of twenty percent or less of mineral oil;
    an approximate proportion of ten percent or less of glycerin;
    an approximate proportion of five percent or less of alcohol;
    an approximate proportion of five percent or less of glyceryl monostearate;
    an approximate proportion of three percent or less of silk extract;
    an approximate proportion of three percent or less of polyoxyethylen stearylether;
    an approximate proportion of two percent or less of methyl paraben;
    an approximate proportion of two percent or less of natural fragrance;
    an approximate proportion of two percent or less of propyl paraben; and
    the balance of the compound in the form of water to complete the compound.

5. A skin care composition, according to claim 4, wherein:
    said approximate proportion or less than five percent of alcohol comprises the use of stearyl alcohol.

6. A skin care composition, according to claim 4, wherein:
    said balance of the compound in the form of water to complete the compound comprises the use of deionized water.

7. A method of treating the skin according to claims 1 or 4 consisting of the steps of;
    applying the skin care compound to the face or hands of the individual;
    massaging gently for increasing the contact of the ingredients of the compound with the skin; and
    rinsing the skin care compound from the skin with cold water.

* * * * *